(12) United States Patent
Nakagomi et al.

(10) Patent No.: US 6,191,281 B1
(45) Date of Patent: Feb. 20, 2001

(54) CRYSTALLINE FUMARATE OF 2-PHENYL-1, 3-THIAZOLIDINE-4-ON DERIVATIVE

(75) Inventors: Kazuya Nakagomi; Tatsuya Kato; Tomokazu Ozaki; Yoshikazu Kumagai, all of Shizuoka-ken (JP)

(73) Assignee: Chugai Seiyaku Kabushiki Kaisha, Tokyo (JP)

( * ) Notice: Under 35 U.S.C. 154(b), the term of this patent shall be extended for 0 days.

(21) Appl. No.: 09/355,243

(22) PCT Filed: Feb. 13, 1998

(86) PCT No.: PCT/JP98/00588

§ 371 Date: Jul. 27, 1999

§ 102(e) Date: Jul. 27, 1999

(87) PCT Pub. No.: WO98/35965

PCT Pub. Date: Aug. 20, 1998

(30) Foreign Application Priority Data

Feb. 14, 1997 (JP) .................................................. 9-68869

(51) Int. Cl.[7] .................................................. C07D 417/12
(52) U.S. Cl. .................................................. 548/186
(58) Field of Search .............................................. 548/186

(56) References Cited

U.S. PATENT DOCUMENTS 5,998,452 * 12/1999 Ohi et al. .............................. 514/369

FOREIGN PATENT DOCUMENTS

0799614A1  10/1997  (EP) .
8-225449   9/1996   (JP) .

OTHER PUBLICATIONS

Tamura et al, European Journal of Pharmacology, 1996, vol. 312, pp. 195–202.

* cited by examiner

*Primary Examiner*—Laura L. Stockton
(74) *Attorney, Agent, or Firm*—Birch, Stewart, Kolasch & Birch, LLP

(57) ABSTRACT

Disclosed are crystals of a compound represented by the formula:

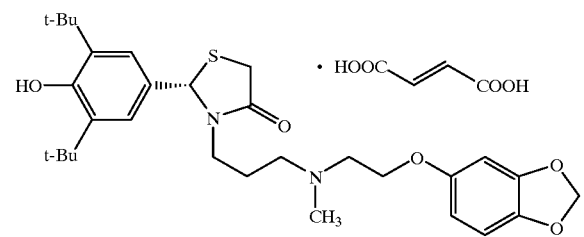

and processes for preparing them.

5 Claims, 6 Drawing Sheets

CRYSTALLINE FUMARATE OF 2-PHENYL-1,3-THIAZOLIDINE-4-ON DERIVATIVE

This application is the national phase under 35 U.S.C. § 371 of PCT International Application No. PCT/JP98/00588 which has an International filing date of Feb. 13, 1998, which designated the United States of America.

FIELD OF THE INVENTION

The present invention relates to crystals of a salt of (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one which are useful as therapeutic agents for ischemic diseases and processes for preparing them.

PRIOR ART

JP No. 7-70023/1995 discloses benzene derivatives which are useful as therapeutic agents for ischemic diseases, especially 2-phenyl-1,3-thiazolidin-4-one derivatives. JP No. 8-225449/1996 discloses therapeutic agents for ischemic diseases containing such a 2-phenyl-1,3-thiazolidin-4-one derivative as an active ingredient. These patent publications disclose (S)-(−)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one as one of such derivatives. However, this compound is an oil around room temperature so that it has problems with handling and storage when it is to be prepared and formulated as a medicament.

A known solution to these problems is conversion of the active ingredient into a salt for ease of handling. We tried to prepare a salt of (S)-(−)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one using various acids, but no salt was obtained in a crystalline form. For example, the hydrochloride of this compound is described in Example 71 of the above-cited patent publication as an example of the salt thereof and generally considered as a stable salt. However, even this salt is amorphous and difficult to purify by crystallization. Therefore, it is not suitable for preparing a medicament since the preparation requires a bulk supply of the compound having a high quality.

An object of the present invention is to provide an acid addition salt which can be purified by crystallization to allow a stable and bulk production of (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one having a high quality, and a process for preparing it.

DISCLOSURE OF THE INVENTION

As a result of extensive research, we found that the fumaric acid salt of (S)-(−)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one can be purified by crystallization among various acid addition salts.

We also found that (S)-(−)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one hydrogen fumarate includes two crystal forms, i.e. low-melting crystal (hereinafter referred to as type I crystal) and high-melting crystal (hereinafter referred to as type II crystal), and that said type II crystal can be obtained by either heating said type I crystal or directly crystallizing said fumarate from a solution.

Accordingly, the present invention provides a crystalline fumaric acid salt of (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one represented by the formula:

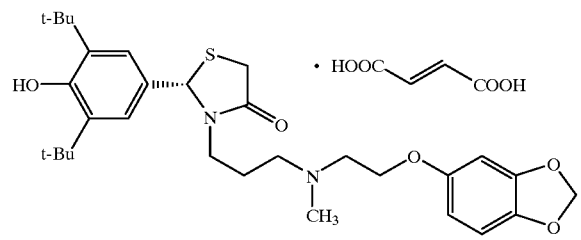

The present invention also provides a process for preparing type II crystals comprising crystallizing (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one hydrogen fumarate from an organic solvent.

The present invention also provides a process for preparing type II crystals comprising heating type I crystals of (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one hydrogen fumarate.

JP No. 8-225449/1996 mentions fumaric acid as an acid capable of forming a salt with 2-phenyl-1,3-thiazolidin-4-one derivatives. However, it merely mentions fumaric acid as one of a number of such acids. It neither discloses nor suggests that (S)-(−)-2-(3,5-di-tert-butyl-4-hydroxyphenyl)-3-[3-N-methyl-N-[2-(3,4-methylenedioxyphenoxy)ethyl]amino]propyl]-1,3-thiazolidin-4-one (hereinafter sometimes referred to as free form) should be chosen from a number of 2-phenyl-1,3-thiazolidin-4-one derivatives to form a salt with fumaric acid and that the resulting fumaric acid salt (hereinafter referred to as compound A) can be purified by crystallization unlike other acid addition salts.

Type I crystal of compound A is a hemi- to mono- hydrate having a melting point of 108–120° C., while type II crystal is an anhydride having a melting point of 142–145° C. According to differential scanning calorimetric analysis (hereinafter abbreviated as DSC), type I crystal shows an endothermic peak around an onset temperature of 105° C. while type II crystal shows an endothermic peak around an onset temperature of 140° C.

Figure 1:
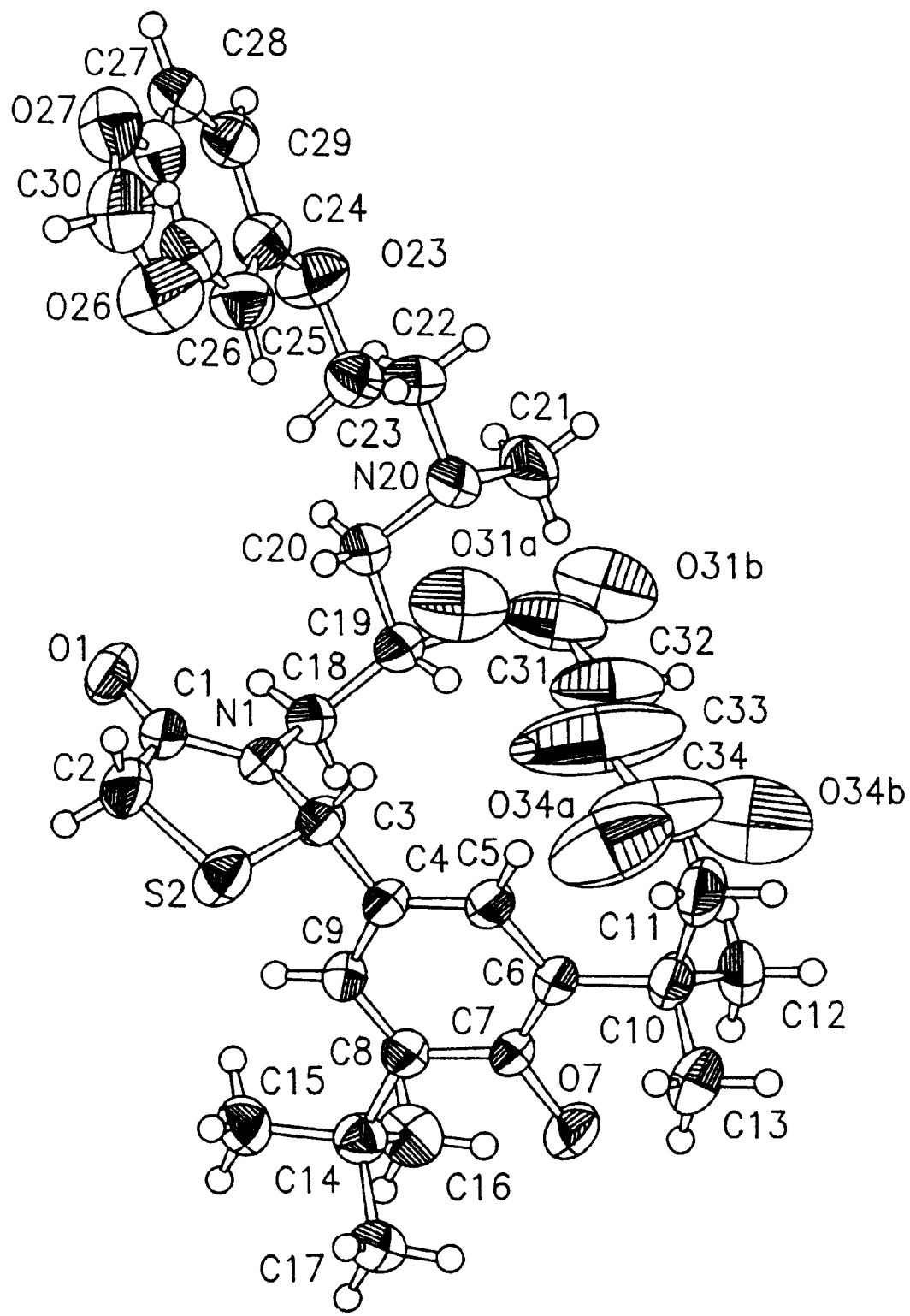
FIG. 1 is a projection showing the molecular structure of type II crystal of compound A.
Figure 2:
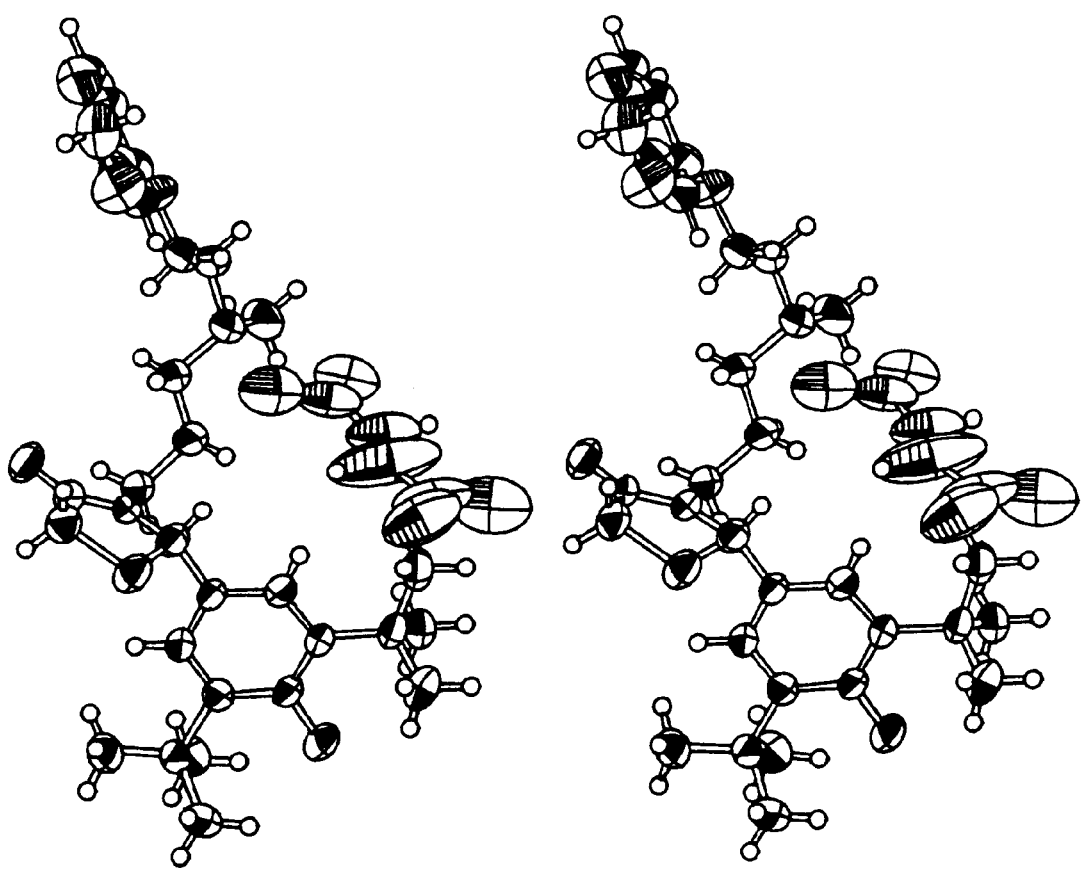
FIG. 2 is a stereographic projection showing the molecular structure of type II crystal of compound A.
Figure 3:
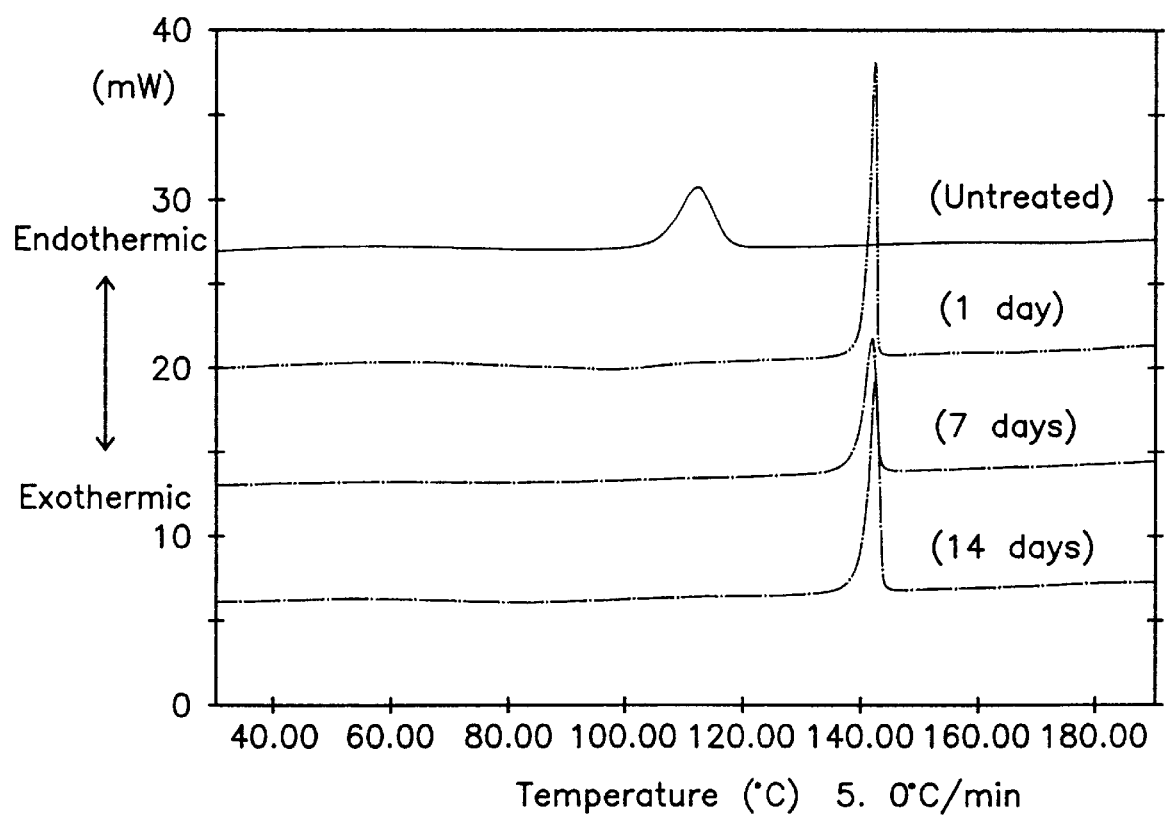
FIG. 3 shows DSC curves of type I crystal of compound A after stored at 80° C. for the indicated periods of days.
Figure 4:
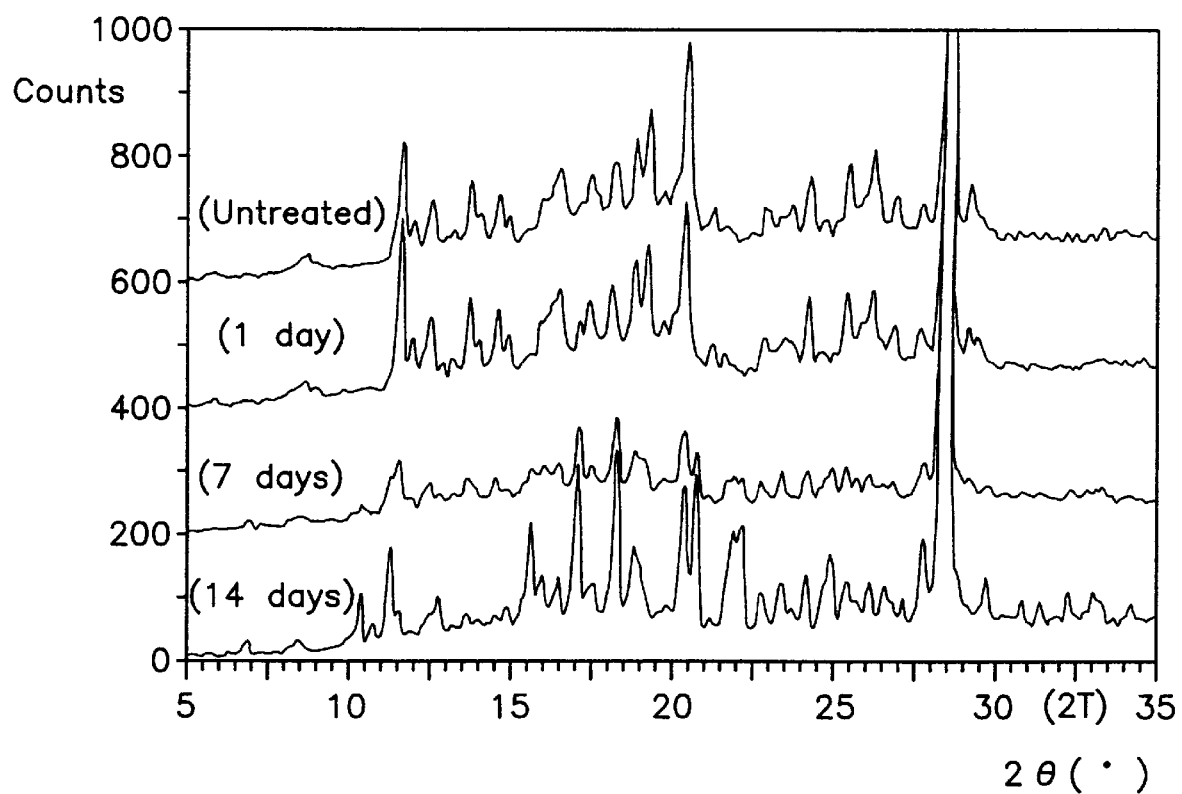
FIG. 4 shows powder X-ray diffraction spectra of type I crystal of compound A after stored at 80° C. for the indicated periods of days.
Figure 5:
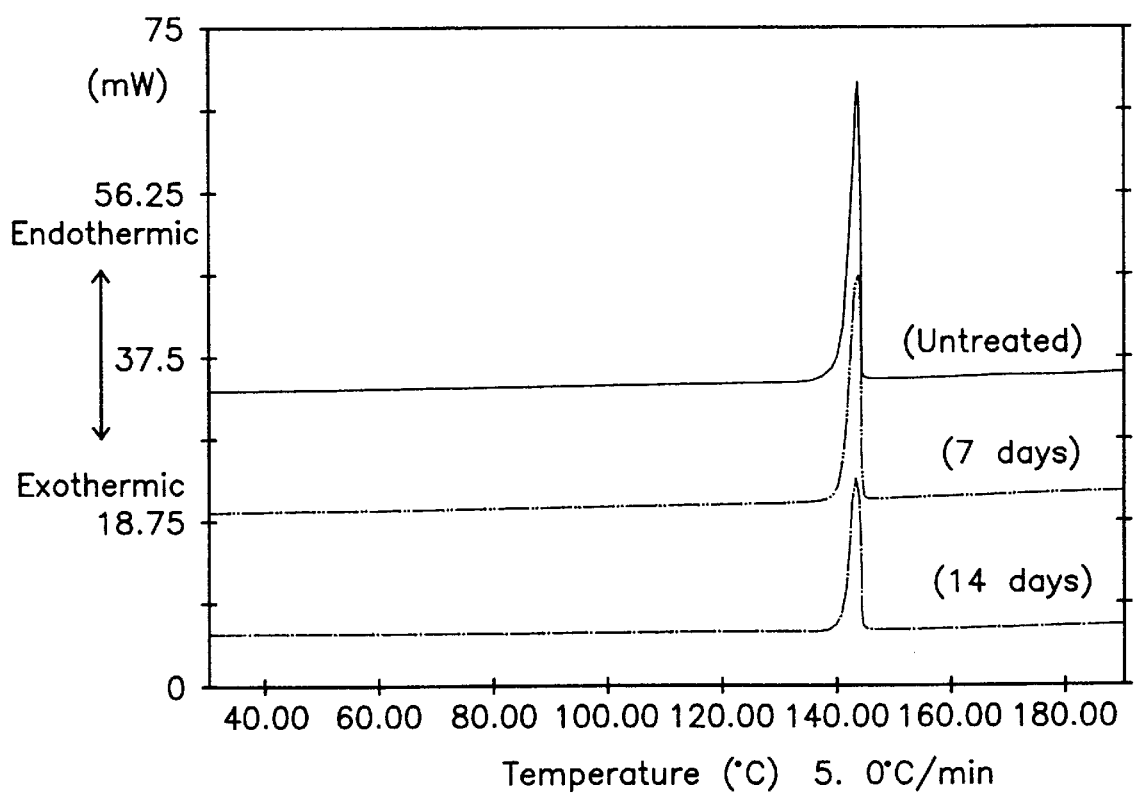
FIG. 5 shows DSC curves of type II crystal of compound A after stored at 80° C for the indicated periods of days.
Figure 6:
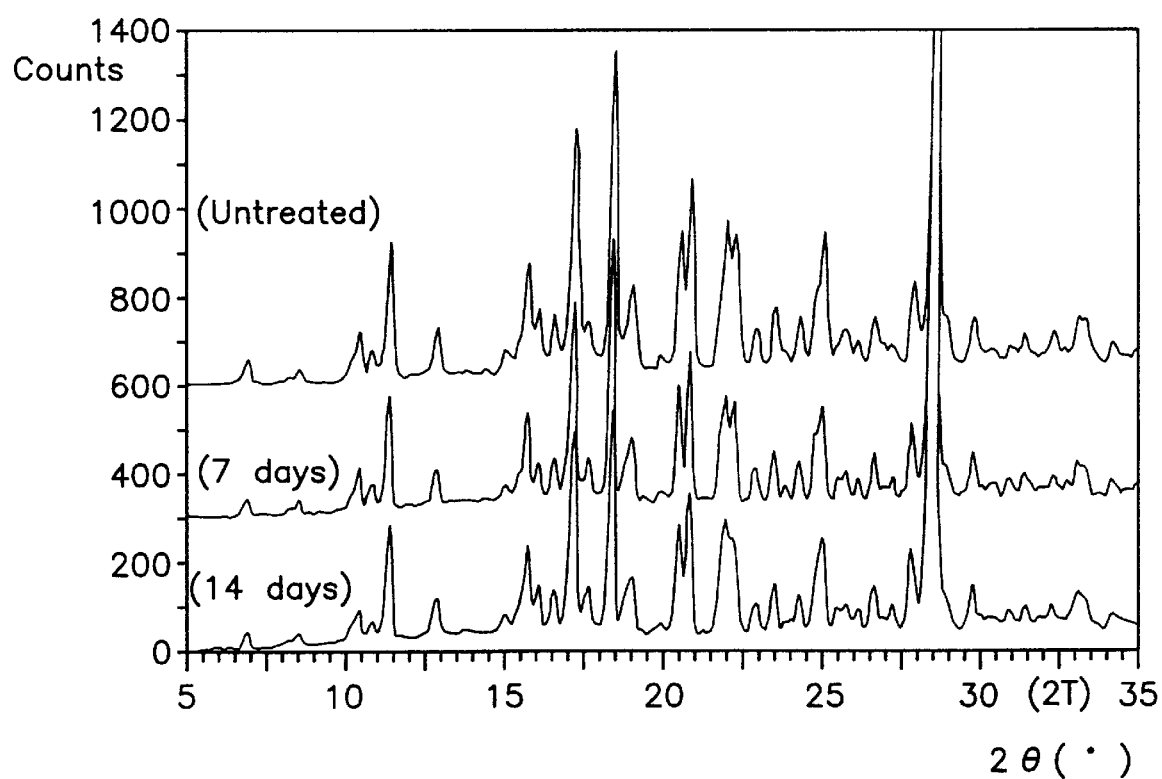
FIG. 6 shows powder X-ray diffraction spectra of type II crystal of compound A after stored at 80° C. for the indicated periods of days.

PREFERRED EMBODIMENTS OF THE INVENTION (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one used in the present invention can be synthesized according to the process described in JP No. 6-206842/1994 or WO95-27710, for example.

Type I crystals of compound A are obtained by mixing the respective solutions of the free form and fumaric acid each dissolved in an alcohol such as ethanol or methanol, concentrating the mixture, adding n-hexane to the residue, cooling the resulting mixture, and then optionally adding diethyl ether to give an amorphous powder of compound A, which is then crystallized from a mixed solvent of a water-miscible organic solvent and a solvent in which compound A is less soluble. The molar ratio between the free form and fumaric acid in the alcoholic solution formed for the preparation of the amorphous powder is generally 1: about 0.50–2.00, preferably 1: about 0.70–1.50, more preferably 1: about 0.80–1.00. The water-miscible organic solvents for crystallizing type I crystal include alcohols such as ethanol, methanol and isopropyl alcohol; tetrahydrofuran; N,N-dimethylformamide; acetonitrile; acetone; and a mixture thereof, preferably ethanol and acetone. The concentration of compound A in the water-miscible organic solvent is generally about 0.1 to about 50 w/v%, preferably about 3 to about 30 w/v%, more preferably about 5 to about 10 w/v%. The solvents in which compound A is less soluble include water and organic solvents including esters such as ethyl acetate; ethers such as diisopropyl ether and tert-butyl methyl ether; hydrocarbons such as benzene, toluene and n-hexane; and a mixture thereof, preferably water and n-hexane. The water necessary for generating type I crystal, which is a hydrate, is supplied by moistures contained as an impurity in the water-miscible organic solvent in many cases, but minor amounts of water should be fed if no or insufficient amounts of moistures are contained in the water-miscible organic solvent. However, it is not necessary to include any moisture in the water-miscible organic solvent if water is used as the solvent in which compound A is less soluble. In that case, the ratio between water and the water-miscible organic solvent is generally 1: about 5–80 v/v%, preferably 1: about 10–50 v/v%, more preferably 1: about 20–40 v/v%. When an organic solvent is used as the solvent in which compound A is less soluble, however, the ratio of said organic solvent to the solution of compound A in the water-miscible organic solvent is generally 1: about 0.1–50 v/v%, preferably 1: about 0.5–10 v/v%, more preferably 1: about 1–5 v/v%. Type I crystals can be precipitated by simply cooling or concentrating thus obtained solution of compound A in a mixed solvent.

In a preferred embodiment, type I crystals are obtained by mixing a solution of 1 part by weight of the free form in about 20–30 parts by volume of ethanol or methanol with a solution of 0.15–0.2 parts by weight of fumaric acid on the basis of the free form in about 100–200 parts by volume of ethanol or methanol, distilling the solvents off, adding about 10–20 parts by volume of hexane, cooling the mixture and optionally adding about 10–20 parts by volume of ether to precipitate an amorphous powder of compound A, which is then dissolved at a ratio of 1 part by weight in about 20 parts by volume of a water-miscible organic solvent such as acetone, ethanol, tetrahydrofuran or acetonitrile, then combined with about 60 parts by volume of water and optionally heated, then stirred at room temperature.

Type II crystals are obtained by mixing the respective solutions of the free form and fumaric acid each dissolved in a non-aqueous organic solvent and concentrating the mixture to give compound A, which is then crystallized from the organic solvent. The molar ratio between free form and fumaric acid in this mixture is generally 1: about 0.50–2.00, preferably 1: about 0.70–1.50, more preferably 1: about 0.80–1.00. The organic solvents here include esters such as ethyl acetate; alcohols such as methanol, ethanol and isopropyl alcohol; tetrahydrofuran; acetonitrile; acetone; and a mixture thereof, preferably ethyl acetate. The concentration of compound A in thus obtained mixture is generally about 10 to about 90 w/v%, preferably about 30 to about 80 w/v%, more preferably about 50 to about 75 w/v%. Type II crystals can be precipitated by simply cooling or concentrating this mixture or adding a solvent in which compound A is less soluble to the mixture without concentrating. The solvents in which compound A is less soluble include ethers such as diisopropyl ether and tert-butyl methyl ether; hydrocarbons such as benzene, toluene and n-hexane, preferably n-hexane. The ratio of said solvent to the solution of compound A is generally 1: about 0.10–10 v/v%, preferably 1: about 0.25–5 v/v%, more preferably 1: about 0.50–2 v/v%.

In a preferred embodiment, type II crystals are precipitated from about 1–5 parts by volume of a solvent such as ethyl acetate after dissolving 1 part by weight of the free form and about 0.2 part by weight of fumaric acid in about 8–10 parts by volume of a solvent such as ethyl acetate, ethanol or methanol and then distilling the solvent off.

Type II crystal can also be obtained by heating type I crystal for a period of time. Heating temperature is generally about 40 to about 160° C., preferably about 60 to about 130° C., more preferably about 70 to about 100° C. Heating period is generally about 1 to about 240 hours, preferably about 2 to about 200 hours, more preferably about 24 to about 180 hours. Heating may take place in the air or in an inert gas such as nitrogen, argon or helium. Transformation from type I crystal to type II crystal can be verified by measuring the melting point of the crystal after heating.

The following examples further illustrate the present invention without, however, limiting the same thereto.

EXAMPLES

Example 1

Preparation of type I crystal of (S)-(−)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one hydrogen fumarate To a solution of (S)-(−)-2-(3,5-di-tert-butyl-4-butyl-4-hydroxyphenyl)-3-[3-[N-methyl-N-[2-(3,4-methylenedioxy-phenoxy)ethyl]amino]propyl]-1,3-thiazolidin-4-one (380 mg, 0.70 mmol) synthesized according to the process described in JP No. 6-206842/1994 in ethanol (10 ml) was added a solution of fumaric acid (65 mg, 0.56 mmol) in ethanol (10 ml) (prepared under preheating) and the mixture was stirred, then the solvent was removed under reduced pressure. The residue was combined with n-hexane and cooled in a freezer for 4 hours, then ether was added. The precipitate was filtered off and dried to give a white amorphous powder of the fumaric acid salt (300 mg). To a solution of this powder (52 mg) in acetone (1 ml) was added water (3 ml), and the mixture was heated under reflux for 10 minutes, then stirred at room temperature overnight. The resulting precipitate was filtered with suction, washed with water and dried to give white crystals (36.5 mg). mp: 109–117° C. Elementary analysis: calculated for $C_{34}H_{46}N_2O_9 \cdot H_2O$: C, 60.34, H, 7.15, N, 4.14; found: C, 60.52, H, 6.84, N, 4.19.

Example 2

Preparation of type II crystal of (S)-(-)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one hydrogen fumarate To a solution of (S)-(-)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one (569 mg, 1.05 mmol) in ethyl acetate (2 ml) was added a solution of fumaric acid (116 mg, 1.00 mmol) in methanol (3 ml) (prepared under preheating) and the mixture was stirred, then the solvent was removed under reduced pressure. The residue was dissolved in ethyl acetate (1 ml) under heating and the mixture was stirred at room temperature for 15 hours. The precipitate was filtered off, washed with ethyl acetate:n-hexane (1:1) and dried to give white crystals (582 mg). mp: 142–144° C.; Elementary analysis: calculated for $C_{34}H_{46}N_2O_9$: C, 61.99, H, 7.04, N, 4.25; found: C, 61.77, H, 7.09, N, 4.07.

Comparative Example

Preparation of Other Acid Addition salts

The procedure of Example 1 was repeated until the step of obtaining an amorphous powder except that fumaric acid was replaced with hydrochloric acid, sulfuric acid, phosphoric acid, methanesulfonic acid, acetic acid, succinic acid, maleic acid, citric acid, D-tartaric acid and L-tartaric acid to give the acid addition salts in the form of oil, but neither amorphous powder nor crystal was obtained. These oily acid addition salts were dissolved under heating in diethyl ether, diisopropyl ether, acetone, ethyl acetate, ethanol, water or a mixed solvent thereof instead of n-hexane in Example 1 and the mixtures were stirred at room temperature overnight, but did not crystallize.

Test Example 1

X-ray Crystal Structure Analysis

Type II crystals of the fumarate (1 mg) were dissolved in ethyl acetate (0.4 ml) in a sample tube. To this solution was added n-hexane (0.1 ml). This sample tube was placed in a vial containing n-hexane (5 ml) and allowed to stand at room temperature for 8 days to form crystals (mp 143–145° C.). A single crystal was chosen from the formed crystals with a polarizing microscope and subjected to an X-ray crystal structure analysis experiment. The result showed that these crystals fall into the orthorhombic crystal system characterized by a space group $P2_12_12_1$ with lattice constants, a=11.863 (2), b=25.798 (2), c=11.348 (2) angstroms, and Z=4. For the purpose of determining the absolute structure, 6060 reflection data were collected including those for Friedel pairs.

Structure analysis was performed as follows. Phases were determined by direct method (SHELXS-86; G. M. Sheldrick, Acta Cryst., A46,467–473, 1990) and non-hydrogen atoms were located by Fourier syntheses. Refinement of the structure excluding active hydrogen atoms by the method of least squares led to a convergence of the reliability factor (R value) to 4.1%. Examination of Bijvoet's inequalities for Friedel pairs showed that the absolute configuration of the asymmetric carbon of the thiazolidine ring is S-configuration.

Test Example 2

Examination of Thermostability by DSC and Powder X-ray Diffraction

Each of type I and type II crystals was stored at 80° C. and subjected to differential scanning calorimetric analysis (DSC) and powder X-ray diffraction after 1, 7 and 14 days to observe heat-induced crystal transformation.

1) DSC

The assay was performed on 5–10 mg of each sample ground in an agate mortar and crimped in a sealed pan.

Instrument: DSC7 (made by Perkin Elmer)
Rate of temperature rise: 5° C./min
Temperature range: 25° C.–190° C.
Purging gas: nitrogen gas 2) Powder X-ray Diffraction The assay was performed on about 10 mg of each sample ground in an agate mortar and flattened with a glass plate on a sample mount (an anti-reflection plate made from silicon).

Instrument: X'PertMPD (made by Philips)

INDUSTRIAL APPLICABILITY

Crystalline fumaric acid salt of (S)-(-)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one of the present invention provides the advantages of an improved purity and stability, and it is useful for preparing medicament or the like containing (S)-(-)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one with easy handling and high quality. Processes for preparing crystals of the present invention allow a stable and bulk production of (S)-(-)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one.

What is claimed is:

1. A crystalline fumaric acid salt of (S)-(-)-2-(3,5-di-tert-butyl-4-hydroxyphenyl)-3-[3-[N-methyl-N-[2-(3,4-methylenedioxyphenoxy)ethyl]amino]propyl]-1,3-thiazolidin-4-one represented by the formula:

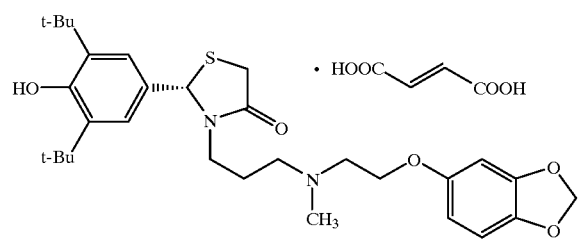

which is type II crystal, said type II crystal has a melting point of about 142 to 145° C.

2. A process for preparing type II crystals of (S)-(-)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one hydrogen fumarate having a melting point of about 142 to 145° C., comprising:

dissolving (S)-(-)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one in a non-aqueous organic solvent;

mixing the solution with a solution of fumaric acid in a non-aqueous organic solvent to form the hydrogen fumarate; and precipitating crystal of said hydrogen fumarate from the mixed solution.

3. The process of claim 2 wherein the organic solvent is selected from an ester, an alcohol, tetrahydrofuran, acetonitrile, acetone and a mixture thereof.

4. The process of claim 3 wherein the organic solvent is ethyl acetate.

5. A process for preparing type II crystals of (S)-(−)-2-(3,5-di-tert-butyl-4-hydroxyphenyl)-3-[3-[N-methyl-N-[2-(3,4-methylenedioxy-phenoxy)ethyl]amino]propyl]-1,3-thiazolidin-4-one hydrogen fumarate having a melting point of about 142 to 145° C., comprising:

heating type I crystals of said hydrogen fumarate in the air or an inert gas to convert said type I crystals having a melting point of about 108 to 120° C. into type II crystal.

* * * * *

UNITED STATES PATENT AND TRADEMARK OFFICE
CERTIFICATE OF CORRECTION

PATENT NO. : 6,191,281 B1
DATED : February 20, 2001
INVENTOR(S) : Kazuya Nakagomi et al.

It is certified that error appears in the above-identified patent and that said Letters Patent is hereby corrected as shown below:

Title page,

Item [54], please change the title of the invention from "CRYSTALLINE FUMARATE OF 2-PHENYL-1,3-THIAZOLIDINE-4-ON DERIVATIVE" to -- CRYSTALLINE FUMARIC ACID SALTS OF A 2-PHENYL-13-THIAZOLIDIN-4-ONE DERIVATIVE AND PROCESSES FOR PREPARING THEM --.

Signed and Sealed this

Thirtieth Day of October, 2001

Attest:

NICHOLAS P. GODICI
Attesting Officer *Acting Director of the United States Patent and Trademark Office*

UNITED STATES PATENT AND TRADEMARK OFFICE
CERTIFICATE OF CORRECTION

| | |
|---|---|
| PATENT NO. | : 6,191,281 B1 |
| DATED | : February 20, 2001 |
| INVENTOR(S) | : Kazuya Nakagomi et al. |

It is certified that error appears in the above-identified patent and that said Letters Patent is hereby corrected as shown below:

<u>Title page,</u>
Item [54], please correct the title from:

"CRYSTALLINE FUMARIC ACID SALTS OF A 2-PHENYL-13-THIAZOLIDIN-4-ONE DERIVATIVE AND PROCESSES FOR PREPARING THEM"

to

-- CRYSTALLINE FUMARIC ACID SALTS OF A 2-PHENYL-1,3-THIAZOLIDIN-4-ONE DERIVATIVE AND PROCESSES FOR PREPARING THEM --.

Signed and Sealed this

Fourteenth Day of January, 2003

JAMES E. ROGAN
*Director of the United States Patent and Trademark Office*